United States Patent [19]

Michel et al.

[11] 4,129,721
[45] Dec. 12, 1978

[54] A-40104 ANTIBIOTICS AND PROCESS FOR PRODUCTION THEREOF

[75] Inventors: Karl H. Michel; Calvin E. Higgens, both of Indianapolis, Ind.

[73] Assignee: Eli Lilly and Company, Indianapolis, Ind.

[21] Appl. No.: 858,505

[22] Filed: Dec. 8, 1977

[51] Int. Cl.$^2$ ............................................. C07G 11/00
[52] U.S. Cl. ...................................... 536/17; 195/81; 560/179; 560/185
[58] Field of Search ......................................... 536/17

[56] References Cited

U.S. PATENT DOCUMENTS 3,949,079  4/1976  Brandi et al. ...................... 424/122

OTHER PUBLICATIONS

Egger, J. Antibiotics, 29, 923–927 (1976).

Primary Examiner—Ethel G. Love
Attorney, Agent, or Firm—Nancy J. Harrison; Arthur R. Whale

[57] ABSTRACT

A-40104 antibiotic complex, comprising active factors A, B, C, and D, produced by submerged aerobic fermentation of *Clitopilus pseudo-pinsitus*. Individual factors, A, B, and C have been isolated. A-40104 factor C is the known antibiotic pleuromutilin. A-40104 factors A and B are novel antibiotics related to pleuromutilin. A-40104 factor A, the major new factor, is the D-xylose acetal derivative of pleuromutilin. A-40104 factors A and B, their 19,20-dihydro derivatives and the per-($C_2$–$C_6$)alkanoyl derivatives of factors A and B and of their 19,20-dihydro derivatives are active against gram-positive and gram-negative bacteria, anaerobic bacteria, and Mycoplasma.

4 Claims, 2 Drawing Figures

A-40104 ANTIBIOTICS AND PROCESS FOR PRODUCTION THEREOF

BACKGROUND OF THE INVENTION

The antibiotic pleuromutilin was isolated in 1951 by Kavanagh et al. [*Proc. Natl. Acad. Soc.* 37, 570–574 (1951)]. The structure of pleuromutilin was later shown to be

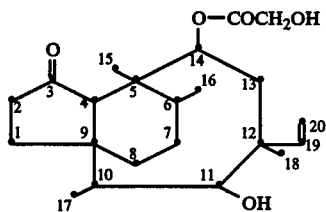

Alkaline hydrolysis of pleuromutilin gives a compound which is known as mutilin. Mutilin has the following structure:

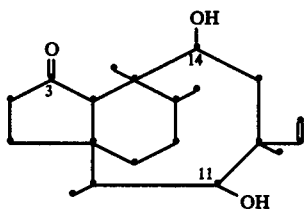

A great number of pleuromutilin derivatives have been prepared [Swiss Pat. No. 572,894 (Derwent No. 26553X); Netherlands Pat. No. 69,11083 (Derwent No. 40,642); Knauseder et al., U.S. Pat. No. 3,716,579; Egger et al., U.S. Pat. No. 3,919,290; Brandl et al., U.S. Pat. No. 3,949,079; Riedl, U.S. Pat. No. 3,979,423; Baughn et al., U.S. Pat. No. 3,987,194; Egger et al., U.S. Pat. No. 4,032,530; K. Riedl, "Studies on Pleuromutilin and Some of Its Derivatives," *J. Antibiotics* 29, 132–139 (1976); H. Egger and H. Reinshagen, "New Pleuromutilin Derivatives with Enhanced Antimicrobial Activity. I. Synthesis," *J. Antibiotics* 29, 915–922 (1976) and "II. Structure-Activity Correlations," ibid., 923–927 (1976); F. Knauseder and E. Brandl, "Pleuromutilins: Fermentation, Structure and Biosynthesis," *J. Antibiotics* 29, 125–131 (1976); J. Drews et al., "Antimicrobial Activities of 81.723 hfu, a New Pleuromutilin Derivative," *Antimicrob. Agents and Chemotherapy* 7, 507–516 (1975).

We have discovered two antibiotics which are new members of the pleuromutilin family of antibiotics. In addition, we have discovered a new method of making pleuromutilin.

DESCRIPTION OF THE DRAWINGS

Infrared absorption spectra of the following A-40104 factors (run in KBr disc) are presented in the accompanying drawings.

SUMMARY OF THE INVENTION

This invention relates to antibiotics. In particular, it relates to an antibiotic complex, the A-40104 antibiotic complex, comprising at least four individual factors, factors A, B, C and D, and to the method of producing this complex by submerged aerobic cultivation of *Clitopilus pseudo-pinsitus* NRRL 11179. A-40104 factors A and B are new antibiotics and are part of this invention. The 19,20-dihydro derivatives of A-40104 factors A and B and the per($C_2$–$C_6$) alkanoyl derivatives of A-40104 factors A and B and of their 19,20-dihydro derivatives are also part of this invention.

A-40104 factors A and B are structurally related to each other and to A-40104 factor C which is the known antibiotic pleuromutilin. At least four antibiotic factors are coproduced during the fermentation to give the A-40104 antibiotic complex of this invention. Pleuromutilin and A-40104 factor A can be separated from the filtered fermentation broth by suitable extraction procedures. A-40104 factor B, a minor factor, can be separated and isolated by chromatographic methods. The other minor factor, A-40104 factor D, can be separated by chromatography, but has not yet been isolated in an amount sufficient for characterization.

DETAILED DESCRIPTION OF THE INVENTION

The following paragraphs describe the physical and spectral properties of A-40104 factors A and B.

A-40104 Factor A

A-40104 factor A crystallizes from chloroform and has a melting point of about 117°–120° C. A-40104 factor A has an empirical formula of $C_{27}H_{42}O_9$, as determined by elemental analysis, and a molecular weight of 510, as determined by field-desorption mass spectrometry.

The ultraviolet absorption spectrum of A-40104 factor A in trifluoroethanol exhibits an absorption maximum at 284 nm ($\epsilon$ 32).

The circular discroism spectrum of A-40104 factor A in trifluoroethanol exhibits the following maxima:
$\Delta\epsilon = +2.84$ at 200 nm
$\Delta\epsilon = +1.72$ at 295 nm.

A-40104 factor A has a specific rotation as follows: $[\alpha]_D^{25} -14°$ (c 1.0, $C_2H_5OH$).

Electrometric titration of A-40104 factor A in 66 percent aqueous dimethylformamide indicates that no titratable groups are present.

Figure 1:
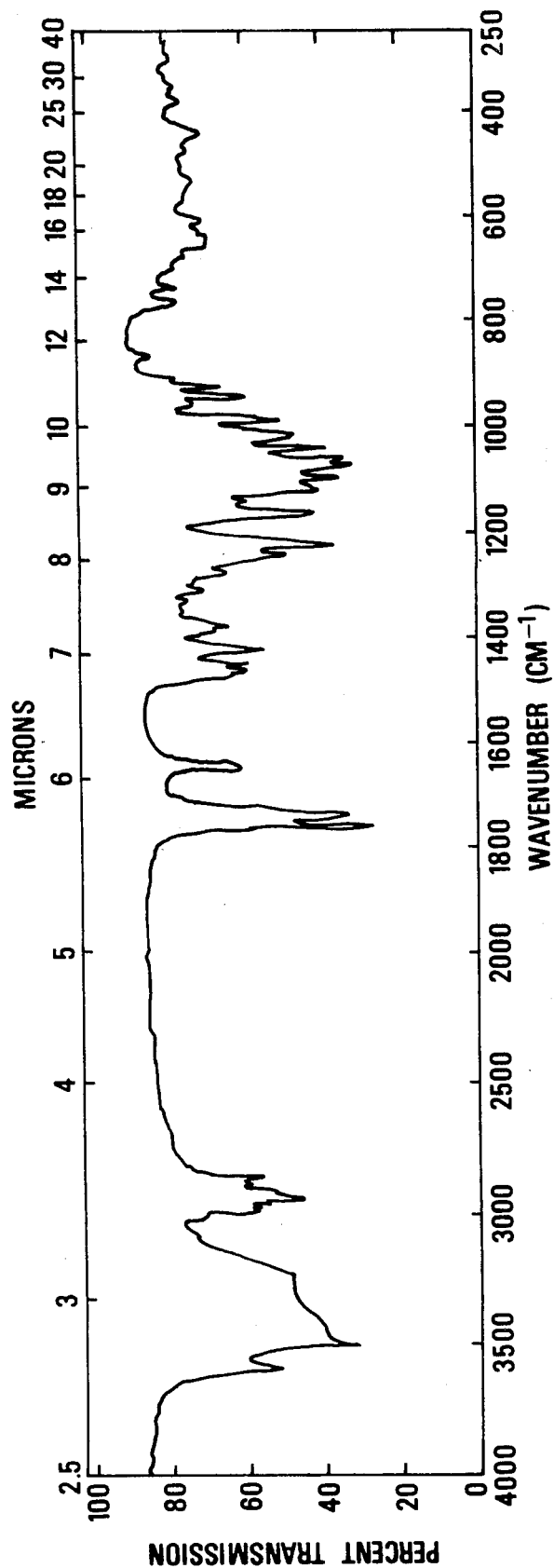
FIG. 1 — A-40104 factor A

The infrared absorption spectrum of A-40104 factor A in KBr disc is shown in FIG. 1 of the accompanying drawings. The most significant absorption maxima occur at the following frequencies ($cm^{-1}$): 3590, 3500, 3450 (broad), 3280 (broad), 2990, 2980, 2960, 2940, 2920, 2890, 2860, 1755, 1735, 1645, 1465, 1447, 1420, 1380, 1330, 1310, 1274, 1240, 1220, 1160, 1117, 1093, 1070, 1060, 1040, 1014, 984, 955, 940, 921, 905, 865, 760, 742, 698, 674, 603, 530 and 442.

A-40104 factor A is soluble in alcohols such as methanol and ethanol, is partially soluble in chloroform and is insoluble in water.

Based on its physical and chemical characteristics, A-40104 factor A is believed to be the β,D-xylopyranosyl acetal derivative of pleuromutilin having the following structure:

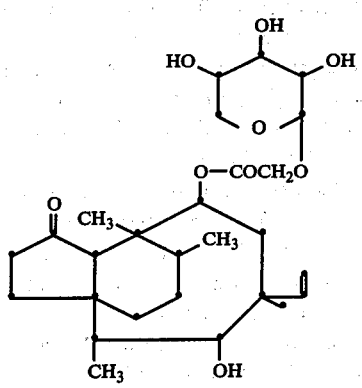

A-40104 Factor B

A-40104 factor B is a white amorphous compound, which occurs as a minor factor in the A-40104 antibiotic complex. It presently represents only about 0.01 to about 0.1 percent of the activity of the A-40104 antibiotic complex. On electron-impact mass spectrometry A-40104 factor B was found to have a molecular weight of 394. Peak matching of the molecular ion and of some of the fragment ions indicates that A-40104 factor B has an empirical formula of $C_{22}H_{34}O_6$. A peak at m/e 318 ($C_{20}H_{30}O_3$) in the mass spectrum of factor B is analogous to a peak at m/e 302 in the pleuromutilin spectrum, indicating that the additional oxygen in factor B is on the nucleus rather than on the side chain. The fragment m/e 163 is common to both factor B and pleuromutilin. A small peak at m/e 245 ($C_{17}H_{25}O$) in the pleuromutilin spectrum is shifted to m/e 261 ($C_{17}H_{25}O_2$) in the factor B spectrum. A-40104 factor B has three hydroxyl groups which are capable of acylation. For example, A-40104 factor B forms a triacetyl derivative on treatment with pyridine and acetic anhydride, giving a compound with the composition $C_{28}H_{40}O_9$ (mol. wt. 520), showing that the additional oxygen function in A-40104 factor B is in a hydroxyl group.

Figure 2:
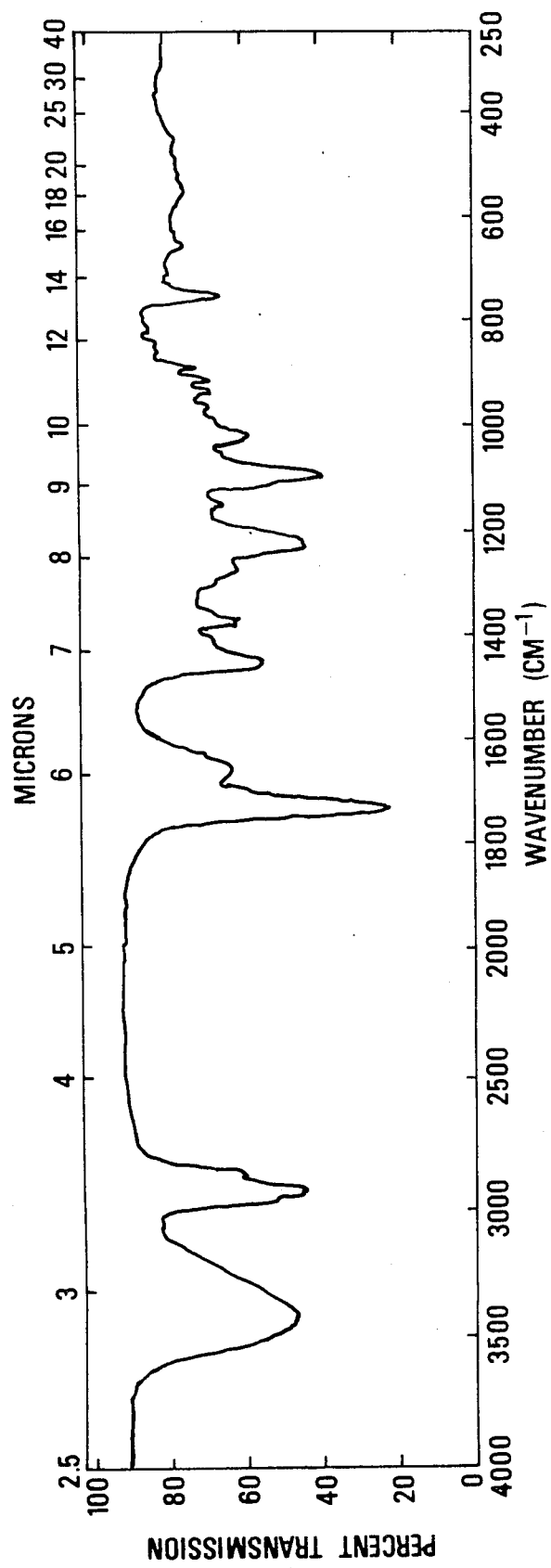
FIG. 2 — A-40104 factor B

The infrared absorption spectrum of A-40104 factor B is shown in FIG. 2 of the accompanying drawings. The most significant absorption maxima occur at the following frequencies (cm$^{-1}$): 3430 (broad), 2940, 2880, 1735, 1660, 1452, 1385, 1375, 1305, 1280, 1233, 1152, 1094, 1020, 997, 967, 933, 912, 888, 752 and 660.

Based on its physical and chemical characteristics, A-40104 factor B is believed to have the following approximate structure:

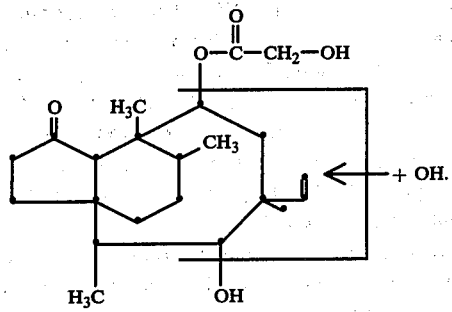

As will be noted, both A-40104 factors A and B contain a vinyl group which can be reduced by standard procedures to give the corresponding 19,20-dihydro derivatives. The 19,20-dihydro-derivatives of A-40104 factors A and B are also active antibacterial agents and are part of this invention.

Both A-40104 factors A and B and their 19,20-dihydro derivatives contain hydroxyl groups which are capable of acylation by standard methods (four hydroxyl groups in the factor A compounds and three hydroxyl groups in the factor B compounds). It will be understood that the peracylated derivatives obtained will have the same acyl group at each position at which acylation can take place (i.e., four in the factor A compounds and three in the factor B compounds). These peracylated derivatives are also antibacterial agents. The per($C_2$-$C_6$) alkanoyl derivatives of A-40104 factors A and B and of the 19,20-dihydro derivatives of A-40104 factors A and B are preferred compounds within this group.

The four individual factors of the A-40104 complex can be separated and identified by chromatographic methods. For example, the factors can be separated by thin-layer chromatography (TLC), using silica gel (Merck Darmstadt) a CHCl$_3$:CH$_3$OH (9:1) solvent system, and *Micrococcus luteus* as a bioindicator. The approximate R$_f$ values of A-40104 factors A-D in this system are given in Table I.

Table I

| A-40104 Factor | R$_f$ Value |
|---|---|
| A | 0.21 |
| B | 0.36 |
| C | 0.52 |
| D | 0.67 |

The factors can also be separated by paper chromatography, using untreated paper (Whatman No. 1), a water saturated with butanol solvent system and *Micrococcus luteus* as a detection organism. The approximate R$_f$ valves of A-40104 factors A-D in this system are given in Table II.

Table II

| A-40104 Factor | R$_f$ Valve |
|---|---|
| A | 0.64 |
| B | 0.51 |
| C | 0.37 |
| D | 0.31 |

Preparation of the A-40104 Antibiotic Complex

This invention also relates to a method of producing A-40104 antibiotic complex, and, thereby, to a method of producing A-40104 factors A and B and the known antibiotic pleuromutilin. This method comprises culturing an A-40104-producing strain of the basidiomycete *Clitopilus pseudo-pinsitus* under submerged aerobic conditions in a suitable culture medium until substantial antibiotic activity is produced. The antibiotic complex and the individual antibiotics are recovered by using various isolation and purification procedures used and understood in the art.

The *Clitopilus pseudo-pinsitus* strain which is useful for production of the A-40104 antibiotics was obtained from the Centraalbureau voor Schimmelcultures (CBS) in the Netherlands. The CBS culture (CBS 270.36) was classified as *Octojuga pseudo-pinsita*. The generic name Clitopilus, which is synonymous with Octojuga, will be used herein to designate the organism. The ability of this culture to produce antibiotics was not known. We discovered its ability to produce the A-40104 antibiotics after an extensive screening procedure.

A *Clitopilus pseudo-pinsitus* strain which is useful for the production of A-40104 factors A and B and pleuromutilin has been deposited and made a part of the stock culture collection of the Northern Marketing and Nutrition Research Division, U.S. Department of Agriculture, Agricultural Research Service, Peoria, Ill. 61604, from which it is available to the public under the number NRRL 11179.

As is the case with other organisms, the characteristics of the A-40104-producing culture, *Clitopilus pseudo-pinsitus* NRRL 11179, are subject to variation. For example, artificial variants and mutants of the NRRL 11179 strain may be obtained by treatment with various known mutagens such as ultraviolet rays, X-rays, high-frequency waves, radioactive rays and chemicals. All natural and artificial variants and mutants which have essentially the same identifying characteristics as *Clitopilus pseudo-pinsitus* NRRL 11179 and produce the A-40104 antibiotics may be used in this invention.

The culture medium used to grow *Clitopilus pseudo-pinsitus* NRRL 11179 can be any one of a number of media. For economy in production, optimal yield, and ease of product isolation, however, certain culture media are preferred. Thus, for example, preferred carbohydrate sources in large-scale fermentation are glucose, tapioca dextrin, starch, and corn oil, although glycerol, maltose, fructose, and the like can also be used. Oleate, laurate and lecithin are other useful sources of carbon. Preferred nitrogen sources are soybean meal, soybean flour, or a dry dog food-yeast combination. Other acceptable nitrogen sources include yeast, cotton seed meal, peanut meal, meat peptone, and dry dog food. Although nutrient inorganic salts are not essential for growth and antibiotic production, soluble salts capable of yielding sodium, magnesium, calcium, ammonium, chloride, carbonate, sulfate, nitrate, and like ions may be added. For example, addition of 0.05% $MgSO_4 \cdot 7H_2O$ and 0.2% $CaCO_3$ to the medium enhances antibiotic production.

Essential trace elements necessary for the growth and development of the organism should be included in the culture medium. Such trace elements commonly occur as impurities in other constituents of the medium in amounts sufficient to meet the growth requirement of the organism.

It may be necessary to add small amounts (i.e., 0.2 ml/l.) of an antifoam agent such as polypropylene glycol to large-scale fermentation media if foaming becomes a problem.

For production of substantial quantities of the A-40104 antibiotics, submerged aerobic fermentation in tanks is preferred. Small quantities of the A-40104 antibiotics may be obtained by shake-flask culture. Because of the time lag in antibiotic production commonly associated with inoculation of large tanks with small amounts of the culture, it is preferable to use a vegetative inoculum that contains larger quantities of cells in an actively growing state. The vegetative inoculum is prepared by inoculating a small volume of culture medium with mycelial fragments of the organism to obtain a fresh, actively growing culture of the organism. The vegetative inoculum is then transferred to a larger tank. The medium used for the growth of the vegetative inoculum can be the same as that used for larger fermentation, but other media can also be used.

The A-40104-producing *Clitopilus pseudo-pinsitus* can be grown at temperatures between about 20° and about 33° C. Optimum A-40104 production appears to occur at temperatures of about 30° C.

As is customary in aerobic submerged culture processes, sterile air is blown through the agitated culture medium. For efficient growth of the organism, there should be sufficient aeration and agitation to maintain a dissolved oxygen level as close to 80% as possible. Lower levels of dissolved oxygen suppress the production of both A-40104 factors A and C, but the effect on factor A is more pronounced.

During the course of fermentation, A-40104 factor C is produced first and A-40104 factor A appears later. The preferred incubation period for production of A-40104 factor A is, therefore, about 12 days. Addition of corn oil to the medium enhances conversion of factor C to factor A during the fermentation. Under conditions which are optimum for A-40104 factor A production, approximately 70 to 90% of antibiotic produced is factor A.

Following their production under submerged aerobic fermentation conditions, the A-40104 antibiotics previously described can be recovered from the fermentation medium by methods used in the fermentation art. The antibiotic activity produced during the fermentation occurs mainly in the broth. Maximum recovery of the A-40104 antibiotics is accomplished, therefore, by a combination of methods, including filtration, extraction of the filtered broth, and absorption chromatography. An especially preferred method is to extract the filtered broth first with toluene and then with chloroform. A-40104 factor C is isolated from the toluene extract, and A-40104 factor A is isolated from the chloroform extract. A-40104 factor B, the minor factor, is separated by absorption chromatography during the purification of A-40104 factor A.

Alternatively, the culture solids, including medium constituents and mycelium, can be used without extraction or separation, but preferably after removal of water, as a source of A-40104 antibiotics. For example, after production of A-40104 antibiotic activity, the culture medium can be dried by lyophilization and mixed directly into feed premix.

In another aspect, after production of A-40104 activity in the culture medium and separation of the mycelium, the filtered broth can be lyophilized to give the A-40104-antibiotic complex in a form which can be used directly in a feed premix.

During the production of the A-40104 antibiotics and the isolation and separation of the individual antibiotic factors, it is preferable to monitor the production and separation processes by chromatographic procedures. For example, a TLC system using a $CHCl_3:CH_3OH$ (9:1) solvent system, silica-gel absorbent, and *Micrococcus luteus* as a bioindicator is preferred.

Activity of the A-40104 Antibiotics

The A-40104 antibiotic complex and individual A-40104 factors A and B inhibit the growth of certain pathogenic organisms, particularly gram-positive bacteria. A-40104 factor A is an especially useful antibacterial agent. The minimal inhibitory concentrations (MIC's) at which A-40104 factor A inhibits selected bacteria, as determined by standard agar-dilution tests, are summarized in Table III.

Table III

| Test Organism | MIC (mcg/ml) A-40104 factor A |
|---|---|
| Staphylococcus aureus 3055 | <0.5 |
| Staphylococcus aureus 3074 | <0.5 |
| Streptococcus faecalis | <0.5 |
| Bordetella bronchiseptica | <0.5 |

In one important aspect of this activity, the A-40104 antibiotics inhibit the growth of organisms which are resistant to other antibiotics. In Table IV the standard disc-plate-assay activity of A-40104 factors A and B against representative organisms is summarized. Activity is measured as the diameter (in mm) of the observed zone of inhibition; the diameter of disc used in each case was 6.35 mm.

Table IV

| Test Organism | Conc. mcg/disc | Zone Diameters (mm) A-40104 factor A | A-40104 factor B |
|---|---|---|---|
| Staphylococcus aureus 3055[1] | 100 | 31.2 | 27.1 |
| Staphylococcus aureus 3055[1] | 10 | 27.2 | 18.9 |
| Staphylococcus aureus 3074[2] | 100 | 29.2 | 25.4 |
| Staphylococcus aureus 3074[2] | 10 | 25.4 | 13.5 |
| Staphylococcus aureus 3130[3] | 100 | 34.0 | 29.5 |
| Staphylococcus aureus 3130[3] | 10 | 29.2 | 19.0 |
| Streptococcus pyogenes[4] | 100 | 27.0 | 23.0 |
| Streptococcus pyogenes[4] | 10 | 21.0 | 19.0 |
| Streptococcus sp. 9960[5] | 100 | 8.7 | 0 |
| Streptococcus sp. 9960[5] | 10 | 0 | 0 |
| Diplococcus pneumoniae | 100 | 20.0 | 17.0 |
| Diplococcus pneumoniae | 10 | 14.0 | 12.0 |

[1] Penicillin-G susceptible
[2] Penicillin-G resistant
[3] Methicillin resistant
[4] Group A
[5] Group D Table V shows that A-40104 factor A compares favorably with ampicillin in a series of in vitro tests using the gradient-plate agar-dilution method.

Table V

| Test Organism | MIC (mcg/ml) A-40104 factor A | Ampicillin |
|---|---|---|
| Streptococcus pyogenes | <0.01 | <0.01 |
| Streptococcus sp. X-66 (Group D) | 0.5 | 0.8 |
| Streptococcus sp. 9960 (Group D) | 70 | 0.6 |
| Neisseria gonorrhea | 0.5 | 0.5 |
| Neisseria gonorrhea Sand. | 0.07 | 0.07 |
| Neisseria gonorrhea Lind. | 0.5 | 0.5 |
| Hemophilus influenzae Brun.[1] | 2 | 0.5 |
| Hemophilus influenzae Dick.[1] | 2 | 0.5 |
| Hemophilus influenzae Laiy.[1] | 4 | 0.5 |
| Hemophilus influenzae 251[2] | 0.7 | 70 |
| Hemophilus influenzae 259[2] | 0.7 | 70 |
| Hemophilus influenzae 260[2] | 0.7 | 70 |

A-40104 factor A and 19,20-dihydro A-40104 factor A (dihydro-A-40104A) have shown in vivo antimicrobial activity against experimental bacterial infections. When two doses of these compounds were administered to mice in illustrative infections, the activity observed was measured as an $ED_{50}$ value [effective dose in mg./kg. to protect 50 percent of the test animals; see Warren Wick, et al., *J. Bacteriol.* 81, 233–235 (1961)]. The $ED_{50}$ values observed for these compounds are given in Tables VI and VII.

Table VI

| | Activity of A-40104 Factor A | | |
|---|---|---|---|
| Test Organism | Route | $ED_{50} \times 2$ | Infecting Challenge |
| Staphylococcus aureus 3055 | sc | 15.7 | 1,260 × $LD_{50}$ (ip) |
| Streptococcus pyogenes C203 | sc | 3.6 | 195 × $LD_{50}$ (ip) |
| Streptococcus pneumoniae Park I | sc | 21.5 | 1,280 × $LD_{50}$ (ip) |

Table VII

| | Activity of Dihydro-A-40104A | | |
|---|---|---|---|
| Test Organism | Route | $ED_{50} \times 2$ | Infecting Challenge |
| Staphylococcus aureus 3055 | sc | ≤4.4 | 69.5 × $LD_{50}$ (ip) |
| Staphylococcus aureus 3055 | oral | 28 | 3,400 × $LD_{50}$ (ip) |
| Staphylococcus aureus 3055 | oral | 27 | 500 × $LD_{50}$ (ip) |
| Streptococcus pyogenes C203 | sc | 5.8 | 1,690 × $LD_{50}$ (ip) |
| Streptococcus pneumoniae Bi-343 | sc | 35 | 30 × $LD_{50}$ (ip) |
| Streptococcus pneumoniae BI-492 | sc | 15.2 | 340 × $LD_{50}$ (ip) |

The A-40104 antibiotics also inhibit the growth of a variety of anaerobic bacteria. Table VIII summarizes the activity of A-40104 factor A, as determined by the standard agar-dilution test.

Table VIII

| Test Organism | MIC (mcg/ml)* |
|---|---|
| Actinomyces israelii | ≤0.5 |
| Clostridium perfringens | 8 |
| Clostridium septicum | 8 |
| Eubacterium aerofacines | 16 |
| Peptococcus asaccharolyticus | ≤0.5 |
| Peptococcus prevoti | ≤0.5 |
| Peptostreptococcus anaerobius | 2 |
| Peptostreptococcus intermedius | ≤0.5 |
| Bacteroides fragilis 111 | 8 |
| Bacteroides fragilis 1877 | 8 |
| Bacteroides fragilis 1936B | 8 |
| Bacteroides thetaiotaomicron | 2 |
| Bacteroides melaninogenicus 1856/28 | 4 |
| Bacteroides Melaninogenicus 2736 | 4 |
| Bacteroides vulgatis | 4 |
| Bacteroides corrodens | 8 |
| Fusobacterium symbiosum | 4 |
| Fusobacterium necrophorum | ≤0.5 |

*MIC determined by the agar-dilution method. Endpoints were read after 24 hours incubation.

A special advantage of the A-40104 antibiotics is that they are relatively nontoxic. For example, the $LD_{50}$'s of A-40104 factor A and the tetraacetyl derivative of A-40104 factor A, on intraperitoneal injection in mice, are greater than 300 mg/kg.

Activity against mycoplasma is an especially important aspect of the antimicrobial activity of the A-40104 antibiotics. Mycoplasma species are pathogenic to man and various animals. Agents active against mycoplasmas are especially needed for the prevention and treatment of mycoplasmal diseases of poultry, swine and cattle.

The minimal inhibitory concentrations (MIC's) of A-40104 factor A; 19,20-dihydro-A-40104 factor A; and the tetraacetyl derivative of A-40104A against various mycoplasma species, as determined by in vitro broth-dilution studies, are summarized in Table IX.

Table IX

| Test Organism | A-40104 factor A | Dihydro- A-40104A | Tetraacetyl A-40104A |
| --- | --- | --- | --- |
| Mycoplasma gallisepticum | ≦0.78 | 0.195 | 12.5 |
| Mycoplasma synoviae | ≦0.78 | 0.195 | 50.0 |
| Mycoplasma hyorhinis | 1.56 | 0.195 | 25.0 |
| Mycoplasma hyopneumoniae | 0.195 | 0.097 | 12.5 |

An important aspect of this invention is the use of the A-40104 antibiotics in the treatment of swine dysentery. As discussed by W. E. Brown et al. in U.S. Pat. No. 4,041,175, pleuromutilin is effective in the treatment of swine dysentery. We have discovered that the A-40104 antibiotics of this invention are also active against *Treponema hyodysenteriae*, the organism most commonly associated with swine dysentery. The activity was determined using an in vitro test which involved incorporating the compound at levels of 50, 5.0, 0.5 and 0.05 mcg/ml in trypticase soy agar plates containg 5% bovine defibrinated blood. The agar surface was inoculated with 0.1 ml of a $10^{-1}$ dilution of a suspension of *T. hyodysenteriae*. Plates were incubated under anaerobic conditions for four days and then evaluated for presence or absence of growth of hemolytic treponema. In this test A-40104 factor A and 19,20-dihydro-A-40104 factor A inhibited growth of *T. hyodysenteriae* at the 50, 5.0 and 0.5 mcg/ml agar concentrations.

When used for the treatment of swine dysentery, the A-40104 antibiotics can be administered to orally to swine infected with the disease in the form of a tablet, capsule, powder or the like. A preferred method of administration, however, is to incorporate the A-40104 antibiotic in the swine feed ration.

Another veterinary aspect of this invention is the activity of the A-40104 antibiotics against *Pasteurella* species. *P. multocida*, for example, is a causative agent of respiratory infection in cattle, poultry, and swine. *P. hemolytica* is a major cause of respiratory disease in cattle. The activity of A-40104 factor A and its dihydro derivative against Pasteurella, as determined by standard in vitro tests, is summarized in Table X.

Table X

| | MIC (mcg/ml) | |
| --- | --- | --- |
| Test Organism | A-40104 factor A | Dihydro- A-40104A |
| Pasteurella multocida (bovine) | 6.25 | 6.25 |
| Pasteurella multocida (turkey) | 12.5 | 12.5 |
| Pasteurella hemolytica | 25.0 | 16.5 |

Another important aspect of this invention is the activity of the A-40104 antibiotics against Spiroplasmas. *Spiroplasma citri* is the causative agent of citrus-stubborn disease; another Spiroplasma, corn-stunt Spiroplasma, affects the growth of corn. In in vitro tests against *Spiroplasma citri* A-40104 factor A and its dihydro derivative inhibit *S. citri* when applied at levels as low as 0.01 ppm.

The A-40104 antibiotics are also active against plant pathogens. For example, when applied either as a foliar spray or as a soil drench, A-40104 factor A is active against powdery mildew. In tests with both bean and barley plants, control of powdery mildew is obtained with a soil drench of A-40104 factor A at a level of 100 ppm, indicating that these compounds have systemic activity. The systemic activity of these antibiotics is especially advantageous in the control of plant pathogens or Spiroplasmas.

In order to illustrate more fully the operation of this invention, the following examples are provided.

EXAMPLE 1

A. Shake-flask Fermentation of A-40104

A mature agar slant culture of *Clitopilus pseudo-pinsitus* NRRL 11179 is scraped with a sterile tool and aseptically transferred to an agar slant having the following composition:

| Ingredient | Amount |
| --- | --- |
| Sucrose | 25 g |
| Blackstrap molasses | 36 g |
| Corn steep liquor | 6 g |
| Malt extract | 10 g |
| $K_2HPO_4$ | 2 g |
| Enzymatically hydrolyzed casein* | 10 g |
| Washed agar | 25 g |
| Deionized water | q.s. 1 liter |

*N-Z Case, Humko Sheffield, Norwich, N. Y.

The inoculated slant is incubated at about 30° C. for about 14 days. The mature slant culture is scraped with a sterile tool, and the macerated mycelia from approximately 5 square centimeters of agar surface is used to inoculate 50 ml of a vegetative medium having the following composition:

| Ingredient | Amount |
| --- | --- |
| Glucose | 10 g |
| Tapioca dextrin* | 10 g |
| Soy hydrolysate powder** | 10 g |
| Brewer's yeast fraction*** | 5 g |
| Tapwater | q.s. 1 liter | pH of medium about 5.3; adjust to pH 6.9 with 5N NaOH

*Stadex 11, A. E. Staley, Decatur, Ill.
**Hysoy T, Humko Sheffield, Norwich, N.Y.
***Amber BYF300, Amber Laboratories, Juneau, Wisc.

The inoculated vegetative medium is incubated in a 250-ml Erlenmeyer flask at about 25° C. for 96 hours on a shaker rotating through an arc two inches in diameter at 250 RPM.

This incubated vegetative medium may be used directly to inoculate the second-stage vegetative medium. Alternatively and preferably, it can be stored for later use by maintaining the culture in the vapor phase of liquid nitrogen. The culture is prepared for such storage in multiple small vials as follows: in each vial is placed 4 ml of incubated vegetative medium and 2 ml of a glycerol-lactose solution having the following composition:

| Ingredient | Amount |
| --- | --- |
| Glycerol | 300 g |
| Lactose | 150 g |
| Deionized water | q.s. 1 liter |

The prepared suspensions are stored in the vapor phase of liquid nitrogen.

A stored suspension (1 ml) thus prepared is used to inoculate 50 ml of a first-stage vegetative medium having the same composition earlier described for the vegetative medium. The inoculated first-stage vegetative medium is incubated in a 250-ml wide-mouth Erlenmeyer flask at 25° C. for about 4 days on a shaker rotating through an arc two inches in diameter at 250 RPM.

B. Tank Fermentation

In order to provide a larger volume of inoculum, 10 ml of the above-described incubated first-stage vegetative medium is used to inoculate 400 ml of a second-stage vegetative growth medium having the same composition as that of the vegetative medium. The second-stage medium is incubated in a 2-liter wide-mouth Erlenmeyer flask at 25° C. for about 48 hours on a shaker rotating through an arc two inches in diameter at 250 RPM.

Incubated second-stage vegetative medium (800 ml), prepared as above described, is used to inoculate 100 liters of sterile production medium having the following composition:

| Ingredient | Amount |
|---|---|
| Glucose | 15 g/l. |
| Glycerol | 5 g/l. |
| Tapioca dextrin | 30 g/l. |
| Dry dog food* | 25 g/l. |
| Yeast extract | 5 g/l. |
| KCl | 1 g/l. |
| $MgSO_4 \cdot 7H_2O$ | 0.5 g/l. |
| $FeSO_4 \cdot 7H_2O$ | 0.1 g/l. |
| $MnCl_2 \cdot 4H_2O$ | 0.05 g/l. |
| $ZnSO_4 \cdot 7H_2O$ | 0.05 g/l. |
| $CaCO_3$ | 0.1 g/l. |
| Deionized water | q.s. 1 liter |
| pH adjusted to 5.0 with 4N HCL | |

*Purina Dog Chow, Ralston Purina Co., St. Louis, Mo. 63188

The inoculated production medium is allowed to ferment in a 165-liter fermentation tank at a temperature of about 30° C. for about 12 days. The fermentation medium is aerated with sterile air, maintaining a dissolved oxygen level of approximately 80%.

EXAMPLE 2

The fermentation is carried out as in Example 1 but using a vegetative medium having the following composition:

| Ingredient | Amount |
|---|---|
| Dextrose | 5 g/l. |
| Galactose | 5 g/l. |
| Glycerol | 5 g/l. |
| Soluble starch | 5 g/l. |
| Yeast extract | 2 g/l. |
| Dry dog food* | 5 g/l. |
| Soybean oil | 2 g/l. |
| Corn oil | 2 g/l. |
| $KH_2PO_4$ | 3 g/l. |
| $MgSO_4 \cdot 7H_2O$ | 0.5 g/l. |
| $FeSO_4 \cdot 7H_2O$ | 0.1 g/l. |
| $CaCO_3$ | 1.0 g/l. |
| $MgCl_2 \cdot 4H_2O$ | 0.05 g/l. |
| $ZnSO_4 \cdot 7H_2O$ | 0.05 g/l. |
| Deionized water | q.s. 1 liter |
| Medium pH about 5.7; adjusted with 4N HCl to pH 5.0 | |

*Purina Dog Chow

EXAMPLE 3

The fermentation is carried out using the method of Example 1, but using a fermentation medium having the following composition:

| Ingredient | Amount |
|---|---|
| Glucose | 50 g/l. |
| Soybean grits | 7.5 g/l. |
| $MgSO_4 \cdot 7H_2O$ | 1.5 g/l. |
| $CaCO_3$ | 2.0 g/l. |
| Deionized water | q.s. 1 liter |
| pH of about 7.4; adjust to pH 6.5 with 4N HCl | |

EXAMPLE 4

Isolation of A-40104 factors A and C

Whole fermentation broth (1200 gallons), obtained by the method described in Example 3, was filtered using a filter aid (Hyflo Super-cel, a diatomaceous earth, Johns-Manville Products Corp.) to give 3640 liters of filtrate. The mycelial cake was washed with deionized water to give an additional 1820 liters of filtrate. The combined filtrate (5460 liters) was extracted at broth pH with toluene (¼ volume) for one hour to give 2500 liters of toluene extract. This toluene extract contained mainly A-40104 factor C (pleuromutilin). The toluene extract was concentrated to a volume of about 23 liters. A first crop of A-40104 factor C (1943 g) crystallized and was recovered by filtration. The mother liquor was concentrated to a volume of about 8 liters. A second crop of factor C (282 g) was separated. The mother liquor was again concentrated to a volume of about 6 liters, chilling at about 4° C. for 72 hours to give an additional 158 g of factor C. The mother liquor from this third crop was concentrated to a viscous oil; this oil was dissolved in diethyl ether (6 liters); the solution was chilled at 4° C. for 72 hours to give a fourth crop (112 g) of A-40104 factor C.

The aqueous solution remaining after the toluene extraction was further extracted with chloroform (¼ volume) for one hour. The chloroform extract obtained was concentrated to a volume of about 10 liters and was chilled at 4° C. for 72 hours. The crystals which formed were separated by filtration and dried to give 588 g of A-40104 factor A.

EXAMPLE 5

Isolation of A-40104 Complex and Individual Factor B

Whole fermentation broth (214 liters), obtained by the method described in Example 1, was filtered using a filter aid to give 119 liters of filtrate. The mycelial cake was washed with water to give an additional 80 liters of filtrate. The combined filtrate (199 liters) was extracted twice at broth pH with ethyl acetate (80 liters each). The combined ethyl acetate extracts were concentrated under vacuum to a volume of about two liters. Hexane (about 20 liters) was added to precipitate the active complex. The precipitated antibiotic complex was separated by filtration, then was redissolved in ethyl acetate (about 300 ml) and reprecipitated with hexane. The precipitate was washed with hexane and dried to give 27.3 g of A-40104 antibiotic complex (containing factors A, B, and C).

A portion of this complex (5 g) was dissolved in chloroform (40 ml). The chloroform solution was filtered, and the filtrate was chromatographed on an open glass column (5.6 × 28 cm) over silica gel (Woelm). The column was slurry packed with chloroform and eluted with chloroform at a flow rate of 2 ml/min, collecting fractions having a volume of 20 ml. At fraction No. 7 the eluting solvent was changed to $CHCl_3:CH_3OH$ (95:5); at fraction No. 28 the solvent was again changed to $CHCl_3:CH_3OH$ (9:1). Fraction nos. 72–120 were combined and evaporated under vacuum to give a dry powder (4 g).

Additional fermentation broth was treated in the same manner to give another 6 g of this material. Chloroform (100 ml) was added to the combined samples (10 g); the material insoluble in chloroform (1.6 g of A-40104 factor A) was separated by filtration. The filtrate was chromatographed on an open glass column (5.8 × 48 cm) over silica gel (Woelm). The column was packed and washed with chloroform and then was eluted with $CHCl_3:CH_3OH$ (97.5:2.5), collecting fractions having a volume of 20 ml at a flow rate of 4 ml/min. Fraction nos. 156–190 were combined and evaporated to dryness under vacuum. The residue was dissolved in a small volume of chloroform; hexane was added to this solution to precipitate the product. The precipitate was separated by filtration and dried to give 99 mg of A-40104 factor B.

EXAMPLE 6

Preparation of 19,20-Dihydro-A-40104 Factor A

Antibiotic A-40104 factor A (10.15 g, 0.0199 mole) was dissolved in tetrahydrofuran (188 ml); 5% Pd/C (2.5 g) was added. The reaction mixture was hydrogenated for 4 hours at room temperature and then was filtered through a sintered-glass funnel with a layer of celite. The filtrate was evaporated under vacuum to dryness. The residue was crystallized from ethyl acetate:methanol (2:1) to give 7.0447 g (0.01375 mole, 69 percent yield) of 19,20-dihydro A-40104 factor A.

EXAMPLE 7

Preparation of 19,20-Dihydro-A-40104 Factor B

A-40104 factor B is hydrogenated, using conditions as described in Example 6, to give 19,20-dihydro-A-40104 Factor B.

EXAMPLE 8

Preparation of Tetraacetyl A-40104 Factor A

A-40104 factor A (2 g) was dissolved in pyridine (5 ml, dry); acetic anhydride (5 ml) was added. The resulting clear solution was allowed to stand at room temperature for 120 hours. The solution was then added to ethanol (20 ml); the resulting solution was evaporated under vacuum until traces of pyridine and acetic acid were removed to give 2.1 g of the tetraacetyl derivative of A-40104 factor A: $[\alpha]_D^{25}$ −22.2° (c 1.0, $C_2H_5OH$); empirical formula $C_{35}H_{50}O_{13}$ and molecular weight 678.325 by peak-matching mass spectrometry.

Anal. Calcd. for $C_{35}H_{50}O_{13}$: C, 62.00; H, 7.40; O, 30.60. Found: C, 62.06; H, 7.32; O, 30.19.

EXAMPLES 9–14

The triacetyl derivative of A-40104 factor B was prepared from A-40104 factor B using a procedure similar to that described in Example 8.

The tetraacetyl derivative of 19,20-dihydro-A-40104 factor A, prepared by reacting 19,20-dihydro-A-40104 factor in the manner described in Example 8.

The triacetyl derivative of 19,20-dihydro-A-40104 factor B, prepared by reacting 19,20-dihydro-A-40104 factor B according to the method of Example 8.

The tetra(n-butyryl) derivative of A-40104 factor A, prepared by reacting A-40104 factor A with n-butyric anhydride according to the procedure of Example 8.

The tripropionyl derivative of A-40104 factor B, prepared by reacting A-40104 factor B with propionic anhydride according to the method of Example 8.

The tetra(n-valeryl) derivative of 19,20-dihydro-A-40104 factor A, prepared by reacting 19,20-dihydro-A-40104 factor A with valeric anhydride according to the method of Example 8.

We claim:

1. A member of the group consisting of (1) antibiotic A-40104 factor A which is the $\beta$,D-xylopyranosyl acetal derivative of pleuromutilin having the following structure:

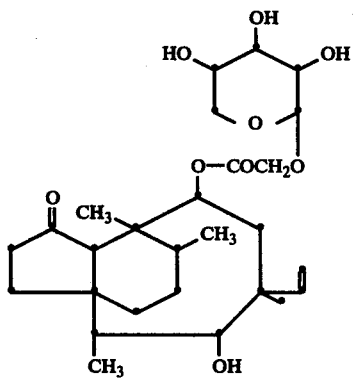

(2) the 19,20-dihydro derivative of A-40104 factor A; and (3) the tetra ($C_2$–$C_6$) alkanoyl derivatives of A-40104 factor A and of 19,20-dihydro A-40104 factor A.

2. The compound of claim 1 which is A-40104 factor A.

3. The compound of claim 1 which is 19,20-dihydro A-40104 factor A.

4. The compound of claim 1 which is the tetraacetyl derivative of A-40104 factor A.

* * * * *